United States Patent
Palmer (10) Patent No.: US 7,818,061 B1
(45) Date of Patent: Oct. 19, 2010

(54) SYSTEMS AND METHODS FOR DETECTING AN ERROR ASSOCIATED WITH AN IMPLANTABLE DEVICE

(75) Inventor: Logan P. Palmer, Santa Monica, CA (US)

(73) Assignee: Advanced Bionics, LLC, Valencia, CA (US)

( * ) Notice: Subject to any disclaimer, the term of this patent is extended or adjusted under 35 U.S.C. 154(b) by 406 days.

(21) Appl. No.: 11/580,498

(22) Filed: Oct. 13, 2006

(51) Int. Cl.
*A61N 1/08* (2006.01)
(52) U.S. Cl. ............................................. 607/32
(58) Field of Classification Search ............... 607/27, 607/31, 32, 55–57, 59–60
See application file for complete search history.

(56) References Cited

U.S. PATENT DOCUMENTS

| | | | | |
|---|---|---|---|---|
| 3,920,025 | A * | 11/1975 | Stasz et al. ............... | 607/61 |
| 4,019,518 | A | 4/1977 | Maurer et al. | |
| 4,232,679 | A | 11/1980 | Schulman | |
| 4,441,210 | A | 4/1984 | Hochmair et al. | |
| 4,532,930 | A * | 8/1985 | Crosby et al. ............. | 607/57 |
| 4,592,359 | A | 6/1986 | Galbraith | |
| 4,612,934 | A | 9/1986 | Borkan | |
| 4,819,647 | A | 4/1989 | Byers et al. | |
| 5,193,539 | A | 3/1993 | Schulman et al. | |
| 5,193,540 | A | 3/1993 | Schulman et al. | |
| 5,292,343 | A | 3/1994 | Blanchette et al. | |
| 5,312,439 | A | 5/1994 | Loeb | |
| 5,314,450 | A | 5/1994 | Thompson | |
| 5,350,407 | A | 9/1994 | McClure et al. | |
| 5,354,319 | A | 10/1994 | Wyborny et al. | |
| 5,501,703 | A | 3/1996 | Holsheimer | |
| 5,522,865 | A * | 6/1996 | Schulman et al. ......... | 607/56 |
| 5,531,774 | A * | 7/1996 | Schulman et al. ......... | 607/56 |
| 5,569,307 | A | 10/1996 | Schulman et al. | |
| 5,603,726 | A * | 2/1997 | Schulman et al. ......... | 607/57 |
| 5,620,472 | A | 4/1997 | Ranbari | |
| 5,876,425 | A * | 3/1999 | Gord et al. ................ | 607/56 |
| 5,938,688 | A | 8/1999 | Schiff | |
| 6,016,449 | A | 1/2000 | Fischell et al. | |

(Continued)

FOREIGN PATENT DOCUMENTS

EP    0177360 B1    4/1986

(Continued)

*Primary Examiner*—George R Evanisko
*Assistant Examiner*—Hiba El-Kaissi
(74) *Attorney, Agent, or Firm*—AdvantEdge Law Group, LLC (57) ABSTRACT

Systems for detecting an error associated with an implantable device include a back-telemetry transmitter within the implantable device configured to transmit one or more signals to an external device having a receiver configured to receive the one or more signals. The implantable device includes circuitry configured to detect an error associated with the implantable device, generate a fault signal corresponding to the error, and turn on the back-telemetry transmitter to transmit the fault signal to the external device. Methods of detecting an error associated with an implantable device include powering up the implantable device with an external device, disabling a back-telemetry transmitter within the implanted device after the implanted device is powered up, detecting an error with the implanted device, generating a fault signal corresponding to the error with the implanted device, turning on the back-telemetry transmitter after the fault signal has been generated, and transmitting the fault signal to the external device with the back-telemetry transmitter.

14 Claims, 7 Drawing Sheets

U.S. PATENT DOCUMENTS

| | | |
|---|---|---|
| 6,051,017 A | 4/2000 | Loeb et al. |
| 6,129,753 A | 10/2000 | Kuzma |
| 6,164,284 A | 12/2000 | Schulman et al. |
| 6,185,452 B1 | 2/2001 | Schulman et al. |
| 6,195,585 B1 * | 2/2001 | Karunasiri et al. ............ 607/57 |
| 6,208,894 B1 | 3/2001 | Schulman et al. |
| 6,219,580 B1 * | 4/2001 | Faltys et al. .................. 607/57 |
| 6,272,382 B1 | 8/2001 | Faltys et al. |
| 6,308,101 B1 | 10/2001 | Faltys et al. |
| 6,329,929 B1 | 12/2001 | Weijand et al. |
| 6,472,991 B1 | 10/2002 | Schulman et al. |
| 6,487,446 B1 | 11/2002 | Hill et al. |
| 6,516,227 B1 | 2/2003 | Meadows et al. |
| 6,539,263 B1 | 3/2003 | Schiff et al. |
| 6,745,077 B1 * | 6/2004 | Griffith et al. ................. 607/61 |
| 6,772,011 B2 | 8/2004 | Dolgin |
| 6,993,393 B2 | 1/2006 | Von Arx et al. |
| 2003/0229383 A1 * | 12/2003 | Whitehurst et al. ........... 607/60 |
| 2005/0216063 A1 | 9/2005 | Hoyme et al. |
| 2005/0283209 A1 | 12/2005 | Katoozi et al. |
| 2006/0030903 A1 | 2/2006 | Seeberger et al. |

FOREIGN PATENT DOCUMENTS

| | | | |
|---|---|---|---|
| WO | WO 9966982 A1 | 12/1999 | |

* cited by examiner

SYSTEMS AND METHODS FOR DETECTING AN ERROR ASSOCIATED WITH AN IMPLANTABLE DEVICE

BACKGROUND

It is often desirable for electronic devices to transmit data, transfer power, or otherwise communicate one with another. Reliable communication is especially important in medical devices, where miscommunication may result in device malfunction and harm to a patient. For example, many implantable medical devices, such as implantable stimulators, are configured to transmit status updates to and receive operational instructions and power from one or more external devices. Without accurate communication, these implantable medical devices could cease to function properly.

An exemplary implantable medical device is an implantable cochlear stimulator (ICS), which may be used to treat sensorineural hearing loss. An ICS seeks to bypass the hair cells in the cochlea, which are essential to hearing but which may not be functioning properly, by presenting electrical stimulation directly to the auditory nerve fibers. The stimulation leads to the perception of sound in the brain and at least partial restoration of hearing function.

Many implantable medical devices are intended to remain permanently in the body of a patient once they are implanted. For this reason, one or more external devices may be configured to communicate with and support an implantable medical device by transmitting various control signals (e.g., stimulation parameters) to the implantable medical device and/or provide power to the implantable medical device. For example, a behind-the-ear (BTE) signal processor may be positioned behind the ear and used to support the ICS by transmitting various stimulation parameters to the ICS and/or providing power to the ICS.

An external device may also be configured to periodically receive status signals from an implantable medical device to ensure that the implantable medical device is functioning properly. To this end, implantable medical devices often include a back-telemetry transmitter configured to transmit one or more status signals to an external device via, e.g., a wireless telemetry link.

However, back-telemetry transmitters often consume a relatively large amount of power. Hence, the current drain on the implantable medical device caused by enabling the back-telemetry transmitter can significantly lower the power supply voltage(s) in the implantable medical device.

In cases where the implantable medical device includes an ICS, the current drain caused by back-telemetry transmitters is often perceptible to the user due to reduced stimulation compliance voltages. To alleviate the reduced compliance voltage levels, the back-telemetry transmitter may be enabled or left "on" at all times. However, this requires additional power to be supplied to the ICS continuously, which may lead to reduced battery life in the BTE signal processor.

Alternatively, the BTE signal processor may temporarily increase the power supplied to the ICS prior to turning on the back-telemetry transmitter in order to alleviate the reduced stimulation compliance voltages. However, such an approach adds undesirable cost and complexity to the system power management hardware and software, induces perceptible noise into the processor audio circuits due to rapidly switching loads on the processor's power supply, and, in some cases, can still cause perceptible fluctuations in the compliance voltage.

SUMMARY

Systems for detecting an error associated with an implantable device include a back-telemetry transmitter within the implantable device configured to transmit one or more signals to an external device having a receiver configured to receive the one or more signals. The implantable device includes circuitry configured to detect an error associated with the implantable device, generate a fault signal corresponding to the error, and turn on the back-telemetry transmitter to transmit the fault signal to the external device.

Methods of detecting an error associated with an implantable device include powering up the implantable device with an external device, disabling a back-telemetry transmitter within the implanted device after the implanted device is powered up, detecting an error with the implanted device, generating a fault signal corresponding to the error with the implanted device, turning on the back-telemetry transmitter after the fault signal has been generated, and transmitting the fault signal to the external device with the back-telemetry transmitter.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Systems and methods for detecting an error associated with an implantable device are described herein. The implantable device may include any device that is implanted within a patient to perform any function. Exemplary, but not exclusive, implantable devices include stimulators, pacemakers, defibrillators, implantable drug delivery systems, sensors, and other types of implantable medical devices. However, for illustrative purposes only, an implantable stimulator will be used to illustrate the exemplary embodiments described herein.

As will be described in more detail below, an exemplary system includes an implantable device and an external device.

The external device includes a forward-telemetry transmitter configured transmit one or more signals to the implantable device. Likewise, the implantable device includes a back-telemetry transmitter configured to transmit one or more signals to the external device via a back-telemetry link. The implantable device includes a number of components configured to allow the implantable device to automatically enable the back-telemetry transmitter and send one or more fault signals to the external device when an error associated with the implantable device is detected.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
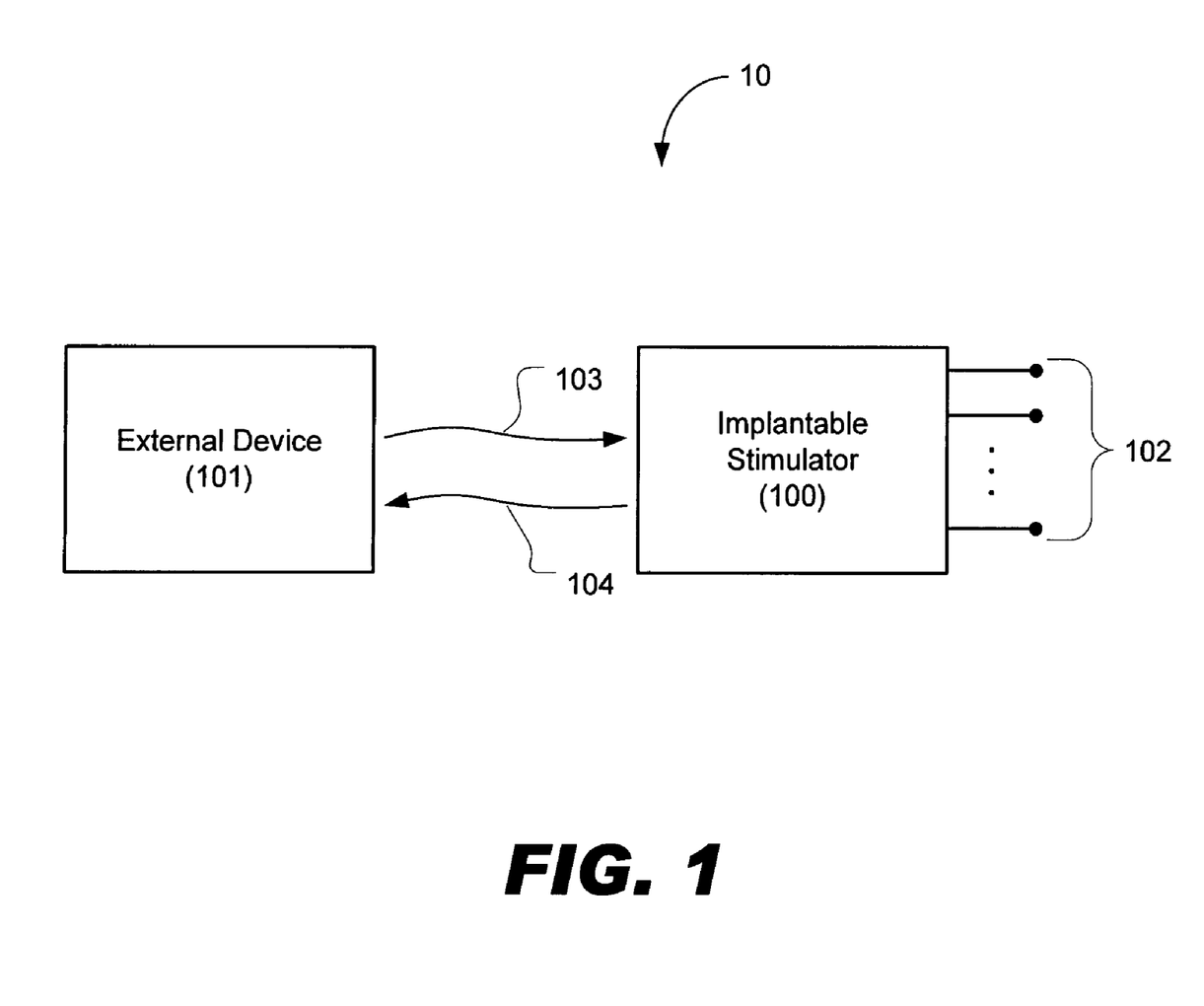
FIG. 1 illustrates an exemplary stimulation system according to principles described herein.

FIG. 1 illustrates an exemplary stimulation system (10). As shown in FIG. 1, the system (10) includes an implantable stimulator (100) configured to communicate with an external device (101) via one or more communication links (103, 104). It will be recognized that the stimulator (100) of FIG. 1 is merely illustrative of the many different types of implantable devices that may be used in connection with the systems and methods described herein.

As shown in FIG. 1, the stimulator (100) may include a number of electrodes (102) that may be configured to apply an electrical stimulation to one or more stimulation sites within a patient. The function of the electrodes (102) will be described in more detail below. The stimulator (100) may additionally or alternatively include one or more catheters (not shown) through which one or more drugs may be infused at one or more stimulation sites.

The external device (101) may include any device configured to communicate with and/or control the implantable stimulator (100). For example, the external device (101) may include, but is not limited to, a BTE signal processor, a programming device, or an external power charger. In some examples, the external device (101) may be configured to transmit control data, stimulation parameters, power signals, and/or other signals to the stimulator (100) via a first communication link (103), also referred to as a forward-telemetry link. Likewise, the implantable stimulator (100) may be configured to transmit status signals and/or other signals to the external device (101) via a second communication link (104), also referred to as a back-telemetry link. In some alternative examples, the first and second communication links (103, 104) may be combined into a single bi-directional communication link.

Before discussing the present systems and methods for monitoring the status of an implantable device, it is helpful to understand the components of a number of exemplary implantable stimulators with which the present systems and methods may be employed.

Figure 2:
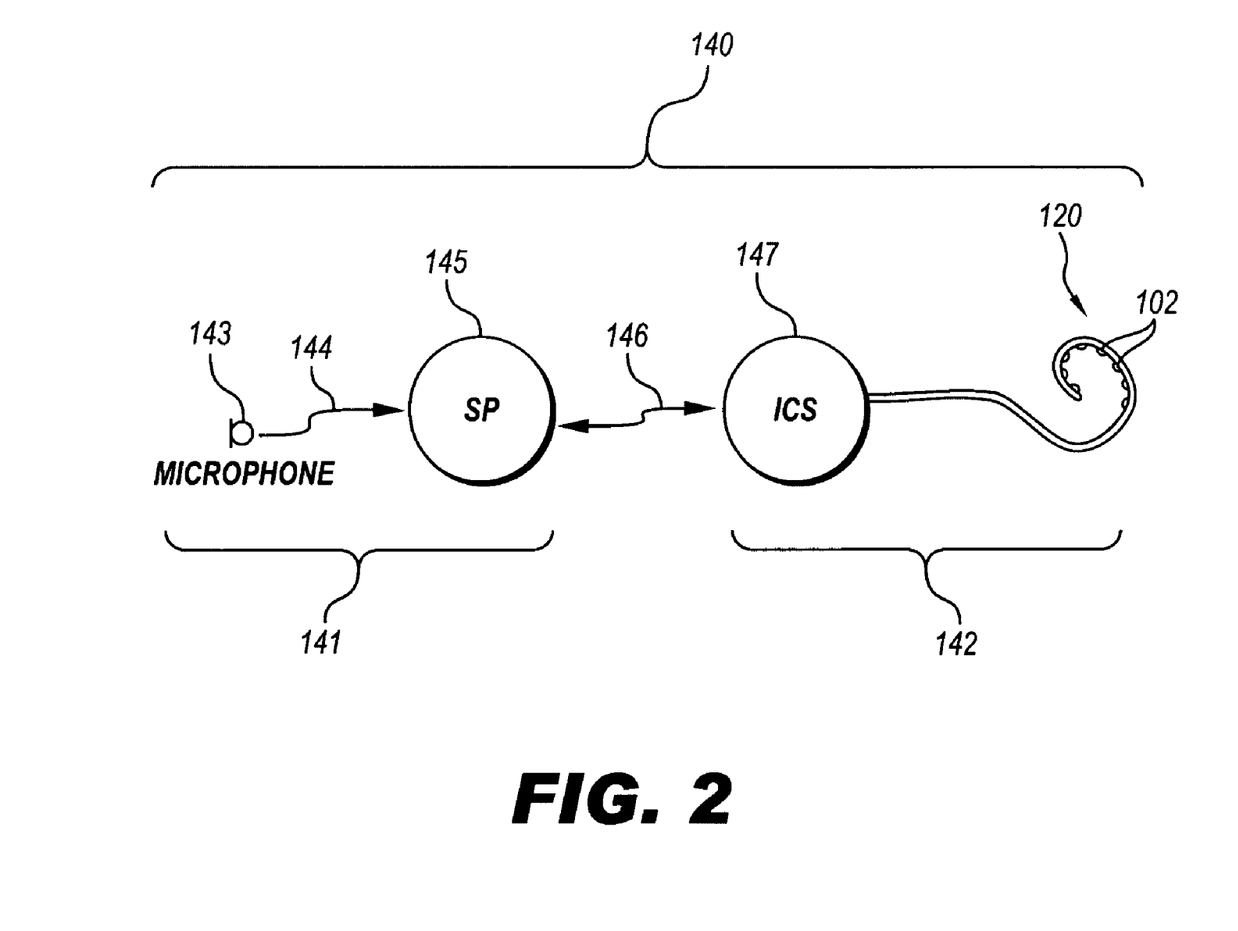
FIG. 2 shows an exemplary cochlear implant system according to principles described herein.

FIG. 2 shows an exemplary cochlear implant system (140) that may be used as an implantable stimulator in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system (140) includes a speech processor portion (141) and a cochlear stimulation portion (142). The speech processor portion (141) may include a speech processor (SP) (145) (e.g., a BTE signal processor), a microphone (143), and/or additional circuitry as best serves a particular application. The cochlear stimulation portion (142) may include an implantable cochlear stimulator (ICS) (147), a number of electrodes (102) disposed on a lead (120), and/or additional circuitry as best serves a particular application. The components within the speech processor portion (141) and the cochlear stimulation portion (142) will be described in more detail below.

The microphone (143) of FIG. 2 is configured to sense acoustic signals and convert such sensed signals to corresponding electrical signals. The electrical signals are sent to the SP (145) via a communication link (144). Alternatively, the microphone (143) may be connected directly to, or integrated with, the SP (145). The SP (145) processes these converted acoustic signals in accordance with a selected speech processing strategy to generate appropriate stimulation parameters for controlling the ICS (147). These parameters may specify or define the polarity, magnitude, location (i.e., which electrode pair or electrode group receive the stimulation current), and timing (i.e., when the stimulation current is to be applied to a particular electrode pair) of the stimulation current that is generated by the ICS (147).

The lead (120) of FIG. 2 is configured to be inserted within a duct of the cochlea. As shown in FIG. 2, the lead (120) includes a multiplicity of electrodes (102), e.g., sixteen electrodes, spaced along its length. The lead (120) may be substantially as shown and described in U.S. Pat. No. 4,819,647 or 6,129,753, each of which is incorporated herein by reference in its respective entirety. Electronic circuitry within the ICS (147) is configured to generate stimulation current via selected pairs or groups of the individual electrodes (102) in accordance with a specified stimulation pattern defined by the SP (145).

The ICS (147) and the SP (145) may be electronically connected via a suitable data or communication link (146). It will be understood that the data communication link (146) may include a bi-directional communication link and/or one or more dedicated uni-directional communication links, such as the forward and back-telemetry links (103, 104) shown in FIG. 1.

In some examples, the SP (145) and the microphone (143) are located comprise an external portion of the cochlear implant system (140) and the ICS (147) and the electrode lead (120) comprise an implantable portion of the system (140) that is implanted within a patient's body. In alternative embodiments, one or more portions of the SP (145) are included within the implantable portion of the cochlear implant system (140).

The external and implantable portions of the cochlear implant system (140) may each include one or more coils configured to transmit and receive power and/or control signals via the communication link (146). For example, the external portion of the cochlear implant system (140) may include an external coil (not shown) and the implantable portion of the cochlear implant system (140) may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system (140). It will be noted that, in some embodiments, both the SP (145) and the ICS (147) may be implanted within the patient, either in the same housing or in separate housings. If the SP (145) and the ICS (147) are in the same housing, the communication link (146) may be realized with a direct wire connection within such housing. If the SP (145) and the ICS (147) are in separate housings, the communication link (146) may include one or more inductive links, for example.

Figures 3A, 3B:
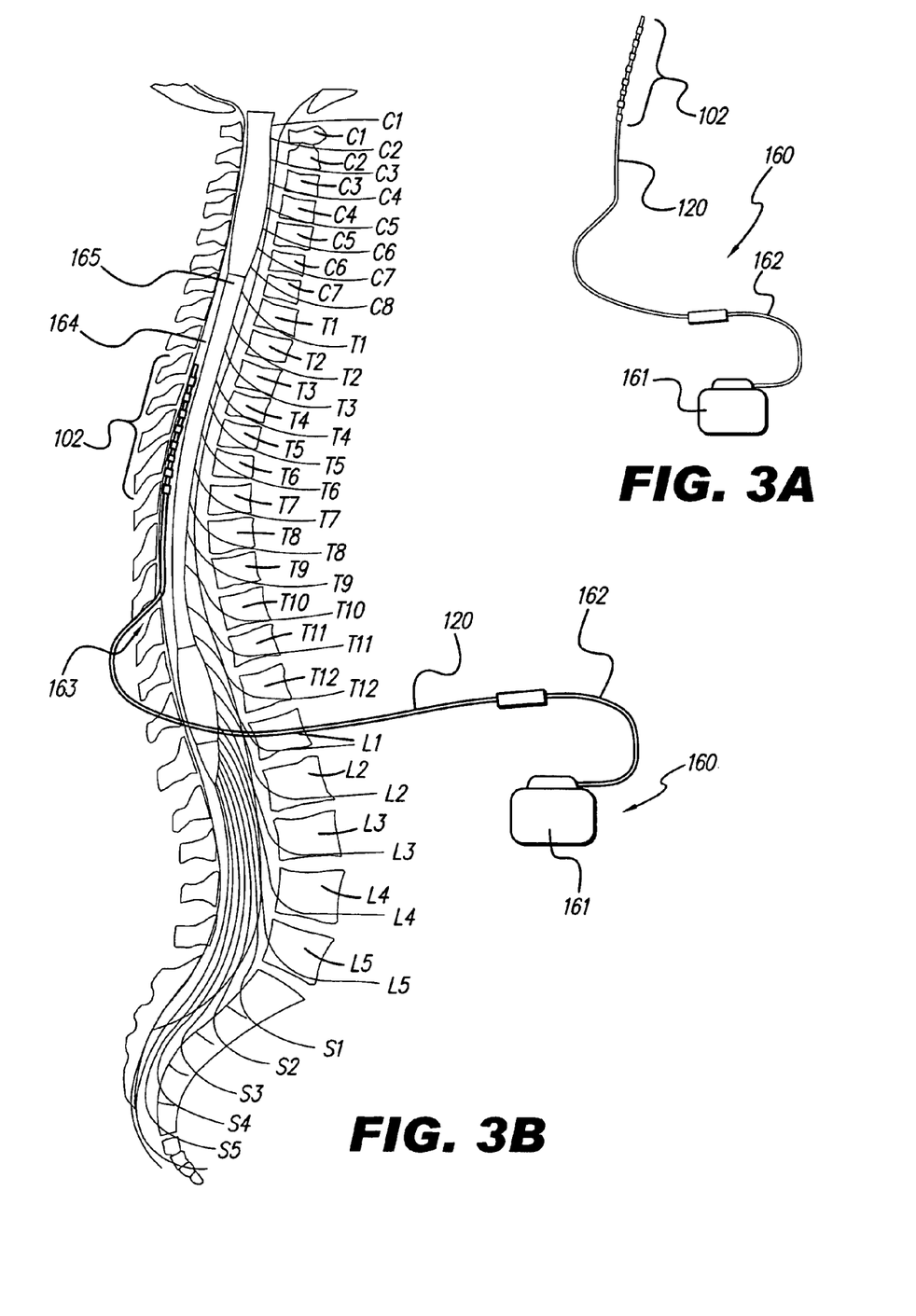
FIGS. 3A and 3B illustrate an exemplary spinal cord stimulator system according to principles described herein.

The implantable stimulator (100) of FIG. 1 may alternatively include a spinal cord stimulator (SCS). FIGS. 3A and 3B illustrate an exemplary spinal cord stimulator system (160). The SCS (160) may be used to treat a number of different medical conditions such as, but not limited to, chronic pain.

As shown in FIG. 3A, the SCS (160) may include an implantable pulse generator (IPG) (161), a lead extension (162), and a lead (120) having an array of electrodes (102) disposed thereon. The electrodes (102) may be arranged, as shown in FIG. 3A, in an in-line array near the distal end of the lead (120). Other electrode array configurations may additionally or alternatively be used. The lead extension (162) need not always be used with the SCS (160), but may be used depending on the physical distance between the IPG (161) and the stimulation site within the patient. The IPG (161) is configured to generate stimulation current pulses that are applied to a stimulation site via one or more of the electrodes (102). Exemplary spinal cord stimulators suitable for use as described herein include, but are not limited to, those disclosed in U.S. Pat. Nos. 5,501,703; 6,487,446; and 6,516,227, all of which are incorporated herein by reference in their respective entireties.

FIG. 3B shows that the array of electrodes (102) of the SCS (160) may be implanted in the epidural space (164) of a patient in close proximity to the spinal cord (165). Because of the lack of space near the lead exit point (163) where the electrode lead (120) exits the spinal column, the IPG (161) is generally implanted in the abdomen or above the buttocks. However, it will be recognized that the IPG (161) may be implanted in any suitable implantation site. The lead extension (162) facilitates implanting the IPG (161) at a location that is relatively distant from the lead exit point (163).

The cochlear implant system (140; FIG. 2) and the SCS (160; FIG. 3A) are merely illustrative of many types of stimulators that may be implanted within a patient and configured to apply one or more stimuli at a stimulation site. For example, the implantable stimulator (100) may additionally or alternatively include a deep brain stimulator, an implantable microstimulator, or any other type of stimulator configured to perform neural response imaging. Exemplary deep brain stimulators suitable for use as described herein include, but are not limited to, those disclosed in U.S. Pat. Nos. 5,938, 688; 6,016,449; and 6,539,263. Exemplary implantable microstimulators, such as the BION® microstimulator (Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 4:
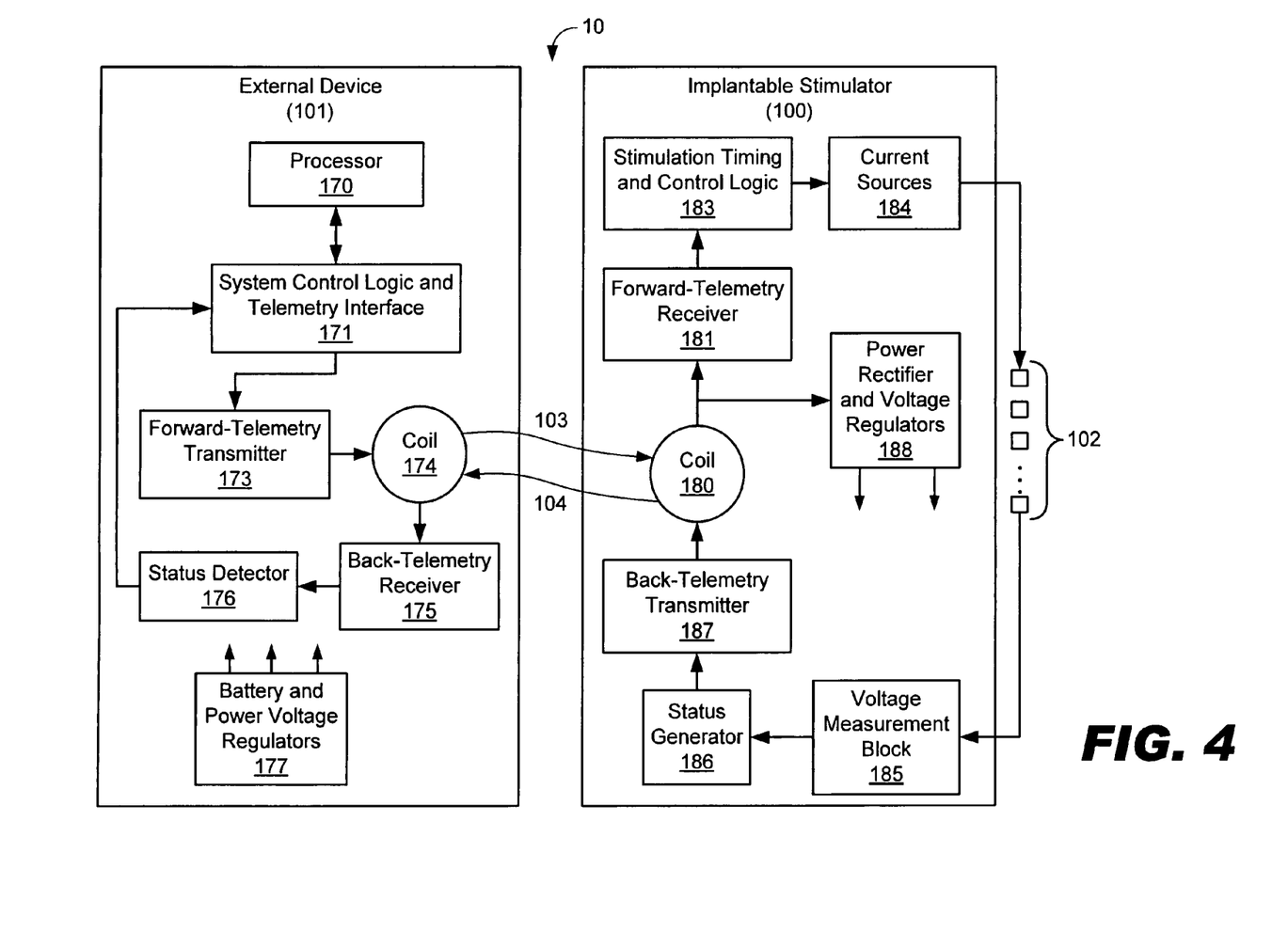
FIG. 4 is a more detailed functional block diagram of the stimulation system shown in FIG. 1 according to principles described herein.

FIG. 4 is a more detailed functional block diagram of the stimulation system (10) shown in FIG. 1. It will be recognized that the stimulation system (10) may be configured to perform additional or alternative functions as best serves a particular application. Moreover, it will be recognized that each of the functional blocks shown in FIG. 4 may include any combination of hardware, software, and/or firmware as best serves a particular application.

As shown in FIG. 4, the external device (101) may include a processor (170) configured to process data that is input into the system. For example, in the case of a cochlear implant system, the processor (170) may be configured to receive and process audio signals. Alternatively, the data may be input manually by a clinician, derived from data transmitted from the implantable stimulator (100), or otherwise provided to the processor (170).

The external device (101) may also include system control logic and a telemetry interface (171). The control logic and telemetry interface (171) may be configured to configure the processed data for transmission via the forward-telemetry link (103) and/or perform other functions within the external device (101).

A forward-telemetry transmitter (173) may be configured to transmit data and/or power signals to the implantable stimulator (100) via the forward-telemetry link (103). In some examples, the external device (101) and stimulator (100) both include one or more coils (174, 180) configured to facilitate wireless communication therebetween. Additionally or alternatively, the external device (101) and stimulator (100) may include one or more alternative means of communication.

The external device (101) may also include a back-telemetry receiver (175) and status detector (176). The back-telemetry receiver (175) may be configured to receive one or more types of data signals from the implantable stimulator (100) via the back-telemetry link (104). For example, as will be described in more detail below, the back-telemetry receiver (175) may receive one or more signals indicating the status of the implantable stimulator (100). The status detector (176) may include one or more components configured to detect the status of the implantable stimulator (100) by processing the received status signals.

The external device (101) may also include one or more battery and power voltage regulators (177). In some examples, the regulators (177) are configured to provide power to one or more of the components within the external device (101). In some examples, the regulators (177) are additionally configured to provide power to the implantable stimulator (100) via the forward-telemetry link (103).

As shown in FIG. 4, the implantable stimulator (100) may include one or more components configured to receive data and/or power signals from the external device (101). In particular, the stimulator (100) may include a forward-telemetry receiver (181) configured to demodulate the digital data stream transmitted by the external device (101). Stimulation timing and control logic (183) may be configured to use the demodulated data signals to drive one or more current sources (184) and cause the current sources (184) to generate stimulation current in accordance with one or more stimulation parameters included within the demodulated data. The stimulation current may then be applied to one or more stimulation sites within the patient via one or more electrodes (102).

In some examples, the stimulator (100) may include a voltage measurement block (185) configured to measure voltages at the electrodes (102) to assess such factors as electrode impedance and evoked neural potentials. The voltage measurement block (185) may additionally or alternatively be configured to measure internal supply voltages of the stimulator (100) for diagnostic and other purposes.

As shown in FIG. 4, the stimulator (100) may also include a status generator (186) configured to generate one or more status signals configured to indicate the status or state of the stimulator (100). For example, the status signals may include, but are not limited to, data indicative of one or more power or voltage levels within the stimulator (100), functionality indicators, errors, and/or any other information regarding the state of the implantable stimulator (100).

In some examples, a back-telemetry transmitter (187) may also be included within the implantable stimulator (100). The back-telemetry transmitter (187) is configured to transmit data to the external device (101) and may be used to transmit one or more of the status signals back to the external device (101). The back-telemetry transmitter (187) will be described in more detail below.

The stimulator (100) may also include one or more power rectifiers and/or voltage regulators (188). In some examples, these components may be configured to extract DC power from one or more power signals received by the coil (180) and supply the DC power to various components within the stimulator (100). The voltage regulators (188) may additionally regulate various power supply voltages within the stimulator (100), including, but not limited to, the compliance voltages used by the current sources (184) and the power used by the back-telemetry transmitter (187).

Figure 5:
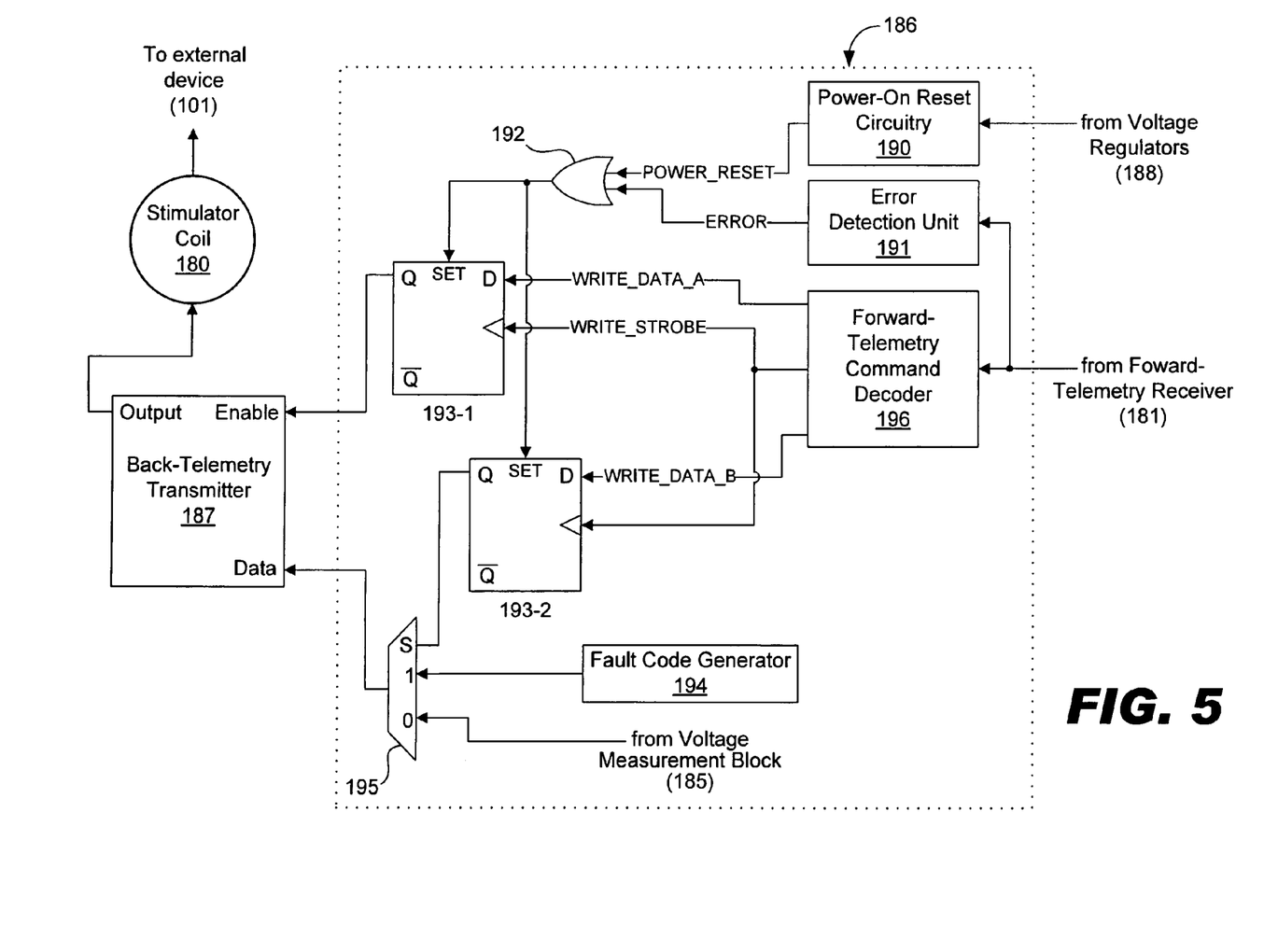
FIG. 5 is a detailed functional block diagram of a status generator and back-telemetry transmitter according to principles described herein.

FIG. 5 is a more detailed functional block diagram of the status generator (186) and back-telemetry transmitter (187). It will be recognized that the status generator (186) and back-telemetry transmitter (187) may be configured to perform additional or alternative functions as best serves a particular application. Moreover, it will be recognized that each of the functional blocks shown in FIG. 5 may include any combination of hardware, software, and/or firmware as best serves a particular application.

As shown in FIG. 5, the status generator (186) may include power-on reset circuitry (190) configured to monitor power voltages in the stimulator (100) and generate a POWER_RESET signal when supply voltages are below acceptable operating limits. The POWER_RESET signal may include any type of signal as best serves a particular application.

An error detection unit (191) may also be included within the status generator (186). The error detection unit (191) is configured to monitor the forward-telemetry data stream and check patterns within the data stream that would indicate either errors in the forward-telemetry link (103) or in the data (e.g., stimulation parameters) sent over the forward-telemetry link (103). If an error is detected, the error detection unit (191) may be configured to generate an ERROR signal.

As shown in FIG. 5, the POWER_RESET and ERROR signals may be combined by an OR gate (192). The output of the OR gate (192) may then be input into a one or more control state flip-flops (193-1 and 193-2), referred to collectively as (193). The flip-flops (193) may include any type of flip-flop. In some examples, as shown in FIG. 5, the flip-flops (193) include D flip-flops.

The flip-flops (193), when set, enable or "turn on" the back-telemetry transmitter (187). Furthermore, the flip-flops (193), when set, select a fault code generated by a fault code generator (194) as the data that is transmitted by the back-telemetry transmitter (187) to the external device (101). In some examples, the fault code is included within a fault signal that is transmitted by the back-telemetry transmitter (187) to the external device (101). The fault code may include sequence of data recognizable by the external device (101) and may be used to indicate any type of error and/or malfunction of the stimulator (100).

In some examples, the fault code is transmitted to the external device (101) during a power-up or start-up procedure. In this manner, the external device (101) may be configured to recognize the fault code at a later point in time.

In some examples, the fault code may be multiplexed with one or more voltage measurements obtained by the voltage measurement block (195). To this end, one or more data multiplexers (195) may be included within the status generator (186). The voltage measurements may be used by the external device (101) to determine optimal stimulation parameters, assess stimulator functionality, or for any other purpose as best serves a particular application.

Hence, one or more of the components shown in FIG. 5 are configured to allow the stimulator (100) to automatically enable the back-telemetry transmitter (187) and send one or more fault status signals to the external device (101) when an error, malfunction, and/or power reset occurs within the stimulator (100). In some examples, the stimulator (100) may automatically enable the back-telemetry transmitter (187) and transmit one or more status signals at any time, even while the stimulator (100) is being powered up after being turned off. Moreover, the stimulator (100) may additionally be configured to automatically cease stimulation if an error or malfunction is detected.

As shown in FIG. 5, a forward-telemetry command decoder (196) may additionally or alternatively be included within the status generator (186). The decoder (196) is configured to decode one or more commands transmitted by the external device (101) to the stimulator (100). For example, the external device (101) may transmit a command to the stimulator (100) to specifically enable or turn on the back-telemetry transmitter (187). The command decoder (196) may decode this command and enable the back-telemetry transmitter (187) accordingly.

Additionally or alternatively, the external device (101) may disable the back-telemetry transmitter (187) by transmitting one or more commands that are decoded by the command decoder (196). For example, the external device (101) may disable the back-telemetry transmitter (187) after processing a fault status signal and performing corrective action related to the fault status signal. In addition, the external device (101) may select alternative sources of data to be transmitted via the back-telemetry transmitter (187) by sending corresponding commands to the command decoder (196).

Figure 6:
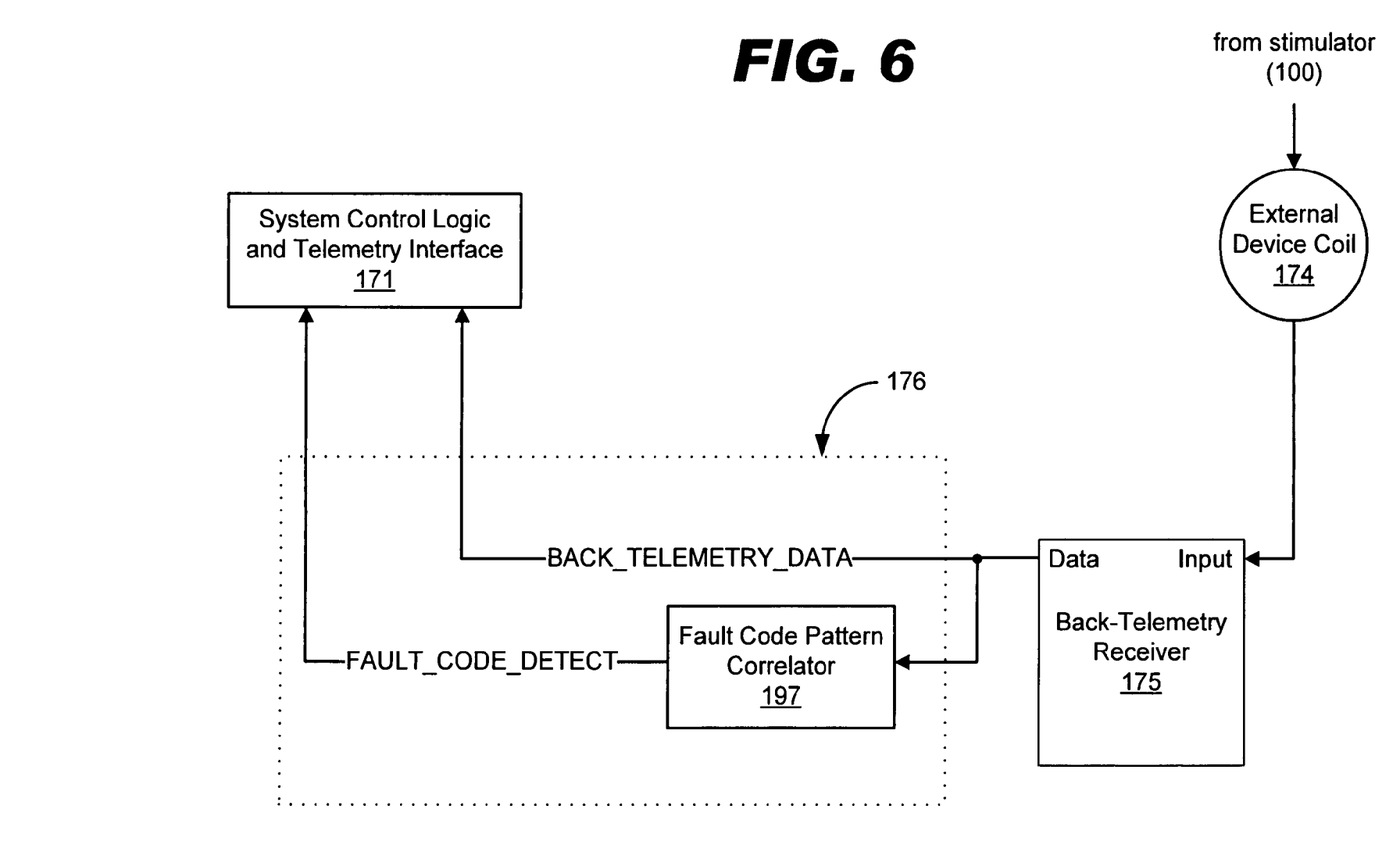
FIG. 6 is a detailed functional block diagram of a back-telemetry receiver and status detector located within the external device according to principles described herein.

FIG. 6 is a more detailed functional block diagram of the back-telemetry receiver (175) and status detector (176) located within the external device (101). It will be recognized that the back-telemetry receiver (175) and status detector (176) may be configured to perform additional or alternative functions as best serves a particular application. Moreover, it will be recognized that each of the functional blocks shown in FIG. 6 may include any combination of hardware, software, and/or firmware as best serves a particular application.

As shown in FIG. 6, the back-telemetry receiver (175) is configured to receive a signal from the implanted stimulator (100) via the coil (174) located within the external device (101). The signal may include, but is not limited to, one or more status signals generated by the status generator (186) within the stimulator (100). In some examples, the back-telemetry receiver (175) is configured to extract a digital data stream from the signal transmitted from the stimulator (100). The extracted data stream is labeled BACK_TELEMETRY_DATA in FIG. 6 for illustrative purposes.

The extracted data stream may be input into the system control logic and telemetry interface (171), as shown in FIG. 6. Additionally or alternatively, the extracted data stream may be input into the status detector (176). In some examples, the status detector (176) includes a fault code pattern correlator (197). The correlator (197) may be configured to compare the extracted data with one or more known fault code patterns. If a match is found, the correlator (197) generates a FAULT_CODE_DETECT signal to indicate that a fault has been detected in the implanted stimulator (100). The FAULT_CODE_DETECT signal is also input into the system control logic and telemetry interface (171) to signal to the external device (101) that a fault has been detected in the implanted stimulator (100).

Hence, the components described in connection with FIGS. 4-6 allow the implantable stimulator (100) to automatically enable the back-telemetry transmitter (187) and transmit a known, recognizable fault code following power-up and whenever an error occurs. The external device (101) is configured to detect the fault code pattern and reboot the stimulator (100) or otherwise remedy the error.

Figure 7:
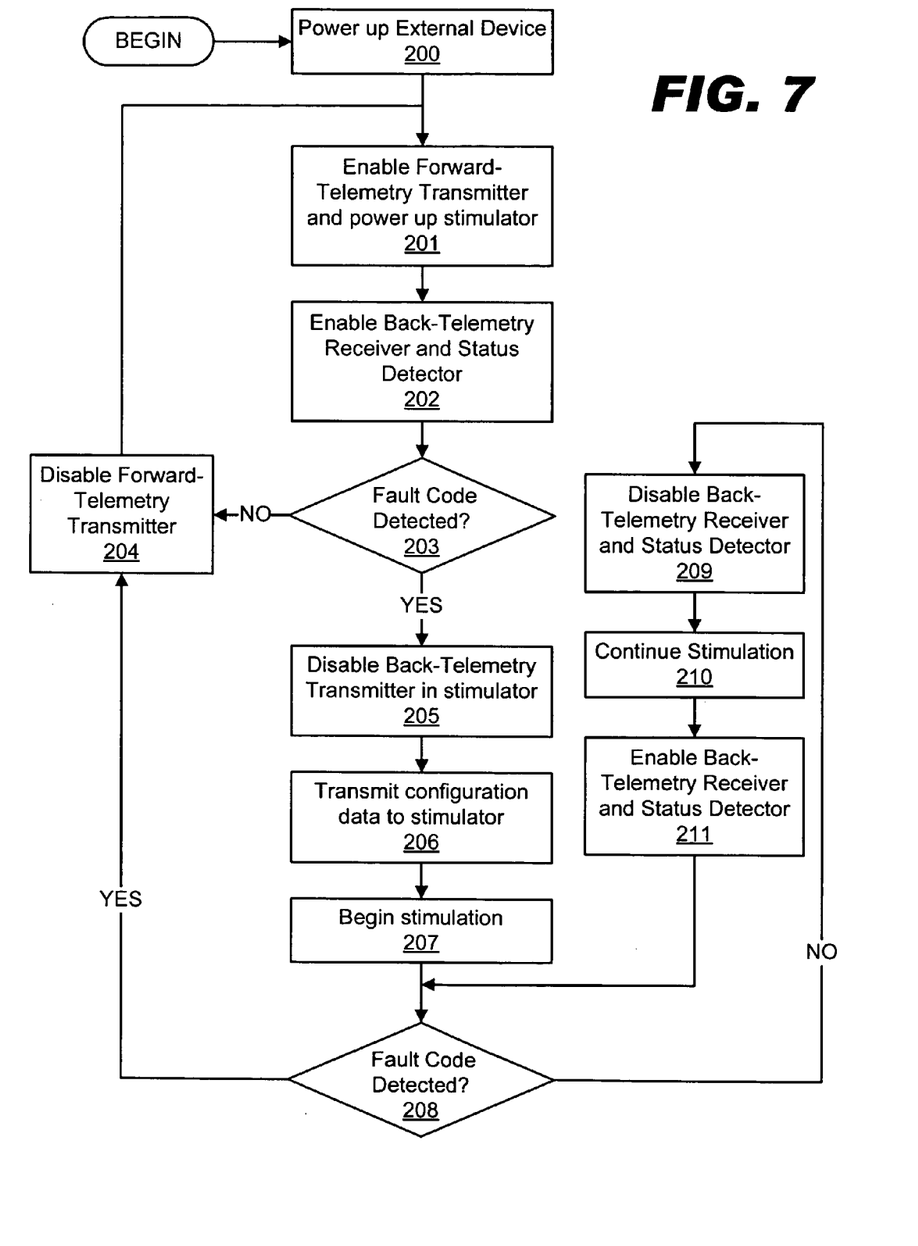
FIG. 7 is a flow chart illustrating an exemplary method of monitoring the status of an implanted stimulator according to principles described herein.

FIG. 7 is a flow chart illustrating an exemplary method of monitoring the status of an implanted stimulator (100). The steps shown in FIG. 7 are merely exemplary and may be modified, reordered, and/or added to as best serves a particular application. In some examples, one or more of the steps included within the flow chart of FIG. 7 are controlled and/or coordinated by the system control logic and telemetry interface (171) included within the external device (101). However, it will be recognized that any other component within the external device (101) and/or the stimulator (100) may additionally or alternatively be configured to control and/or coordinate one or more of the steps shown in FIG. 7.

As shown in FIG. 7, the external device (101) is first powered up (step 200). The external device (101) then enables its forward-telemetry transmitter (173) and powers up the stimulator (100) (step 201). As used herein, with reference to the components and/or devices shown in FIGS. 1-6, the term "enable" will used to refer to any action that "turns on," supplies power to, or otherwise causes a particular component and/or device to function. With the forward-telemetry transmitter (173) enabled, the external device (101) may supply power to the implantable stimulator (100) via the forward-telemetry link (103).

After a period of time, the external device (101) enables its back-telemetry receiver (175) and status detector (176). It will be understood that if the stimulator (100) has powered up correctly, its back-telemetry transmitter (187) may be configured to automatically transmit a fault code. The back-telemetry receiver (175) and status detector (176) may then attempt to detect the fault code transmitted by the stimulator (100) in order to verify a successful power up of the stimulator (100) (step 203).

If the fault code is not detected (No; step 203), the status detector (176) indicates that the stimulator (100) has not powered up as expected. Such a failure in power-up of the stimulator (100) may be caused by the coils (174, 175) being misaligned and/or being too far away from each other. The failure in power-up may additionally or alternatively be caused by any other device malfunction or error.

Once it has been determined that the stimulator (100) has not powered up correctly, the external device (101) may then temporarily disable its forward-telemetry transmitter (173) (step 204). In this manner, the stimulator (100) is powered down. Steps 201-204 are then repeated in an attempt to reboot the stimulator (100) and elicit the fault code from the stimulator (100).

If the fault code is detected (Yes; step 203), the external device (101) recognizes that the stimulator (100) has powered up correctly. The back-telemetry transmitter (187) within the stimulator (100) is then disabled (step 205) to conserve power. In some examples, the external device (101) is configured to disable the back-telemetry transmitter (187) by sending a command via the forward-telemetry link (103) as described previously. Additionally or alternatively, the stimulator (100) may be configured to automatically disable the back-telemetry transmitter (187) once the fault code has been detected. The back-telemetry transmitter (187) may alternatively be manually disabled by a clinician or by the patient.

The external device (101) may then transmit configuration data, one or more stimulation parameters, and/or other control data to the stimulator (100) via the forward-telemetry link (103) (step 206). The stimulator (100) may then begin stimulation (step 207). It will be recognized that the external device (101) may be configured to periodically or continuously transmit data including, but not limited to, one or more stimulation parameters to the stimulator (100) while the stimulator (100) is operating.

If the stimulator (100) detects an error, it may be configured to automatically enable the back-telemetry transmitter (187) and transmit a fault code via the back-telemetry link (104) to the external device (101). The error may include an error in one or more voltage levels, an error in the forward-telemetry data, a power reset of the stimulator (100), or any other error or malfunction of the stimulator (100). In some examples, the stimulator (100) may additionally be configured to cease stimulation when an error is detected. In some examples, the external device (101) may be configured to specify the types of errors that result in the fault code being generated. Moreover, different fault codes corresponding to different types of errors may be generated and transmitted by the stimulator (100).

During the course of stimulation, the external device (101) periodically enables its back-telemetry receiver (175) and status detector (176) and attempts to detect a fault code. In some alternative embodiments, only the back-telemetry receiver (175) is initially enabled. If a fault code is detected, the external device (101) enables the status detector (176) in order to process the fault code.

Hence, as shown in step 208, if a fault code is not detected (No; step 208), the back-telemetry receiver (175) and status detector (176) are disabled to conserve power. Alternatively, the back-telemetry receiver (175) and status detector (176) may remain constantly enabled. Stimulation continues for a period of time (step 210) after which the external device (101) again enables its back-telemetry receiver (175) and status detector (176) and attempts to detect a fault code. Steps 208-211 are repeated until a fault code is detected (Yes; step 208), indicating that an error has occurred within the stimulator (100). The forward-telemetry transmitter (204) within the external device (101) may then be disabled (step 204) and the stimulator (100) rebooted. Alternatively, the external device (101) may remedy the error by, for example, sending one or more corrective signals to the stimulator (100). If a fault code is never detected, steps 208-211 are repeated indefinitely until a user turns off the external device (101) or until the power supply is diminished.

As mentioned, the external device (101) may be configured to specifically enable or turn on the back-telemetry transmitter (187). In some examples, the back-telemetry transmitter (187) may be enabled to perform diagnostic functions such as status register reading, measurement of stimulator supply voltages, measurement of electrode impedance, and neural response imaging (NRI).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
    an implantable device comprising a back-telemetry transmitter configured to transmit one or more signals; and an external device comprising a receiver configured to receive said one or more signals transmitted by said back-telemetry transmitter;

wherein said external device
- powers up said implantable device,
- verifies functionality of said implantable device by detecting a fault signal transmitted by said back-telemetry transmitter, and
- disables said back-telemetry transmitter after the functionality of said implantable device is verified; and wherein said implantable device comprises circuitry that
- transmits said fault signal with said back-telemetry transmitter to said external device when said external device powers up said implantable device;
- detects an error associated with said implantable device while the back-telemetry transmitter is disabled;
- generates another fault signal when said error is detected;
- enables said disabled back-telemetry transmitter when said error is detected; and
- transmits said another fault signal with said enabled back-telemetry transmitter to said external device; and
- disables the back-telemetry transmitter after the another fault signal is received by the external device.

2. The system of claim 1, wherein said external device comprises:
- a status detector configured to detect one or more fault codes contained within said another fault signal; and
- circuitry configured to use said one or more fault codes to remedy said error.

3. The system of claim 2, wherein said external device is configured to remedy said error by rebooting said implantable device.

4. The system of claim 1, wherein said external device is configured to periodically turn on said receiver to detect a presence of said another fault signal.

5. The system of claim 1, wherein said error comprises at least one or more of an error in one or more voltage levels, an error in data transmitted from the external device, a power reset of said implantable device, and a malfunction of one or more components within said implantable device.

6. The system of claim 1, wherein said implantable device comprises an implantable stimulator.

7. The system of claim 6, wherein said implantable stimulator is configured to automatically cease stimulation when said error is detected.

8. The system of claim 1, wherein said implantable device comprises an implantable cochlear stimulator and wherein said external device comprises a speech processor.

9. An implantable device, comprising:
- a back-telemetry transmitter that transmits a fault signal and another fault signal to an external device via a back-telemetry link, wherein the fault signal is transmitted when the external device powers up the implantable device and is for the external device to verify a successful power up of the implantable device; and
- a status generator communicatively coupled to said back-telemetry transmitter and that
  - disables the back-telemetry transmitter after the fault signal is transmitted to the external device,
  - detects an error associated with the implantable device while the back-telemetry transmitter is disabled,
  - generates the another fault signal when the error is detected,
  - enables the disabled back-telemetry transmitter when said error is detected,
  - causes the enabled back-telemetry transmitter to transmit the another fault signal to the external device, and
  - disables the back-telemetry transmitter after the another fault signal is received by the external device.

10. The implantable device of claim 9, further comprising:
- a forward-telemetry receiver configured to receive a number of signals from said external device;
- wherein one or more of said signals are configured to remedy said error.

11. The implantable device of claim 10, wherein said one or more of said signals are configured to remedy said error by rebooting said implantable device.

12. The implantable device of claim 9, wherein said error comprises at least one or more of an error in one or more voltage levels, an error in data transmitted from the external device, a power reset of said implantable device, and a malfunction of one or more components within said implantable device.

13. The implantable device of claim 9, further comprising one or more components configured to apply at least one stimulus at a stimulation site within a patient.

14. The implantable device of claim 13, wherein said one or more components are configured to automatically cease applying said stimulus when said status generator detects said error.

* * * * *